United States Patent [19]
Kok et al.

[11] 4,047,893
[45] Sept. 13, 1977

[54] APPARATUS FOR MEASURING THE ALCOHOL CONTENT IN HUMAN BREATH

[75] Inventors: Bob Kok; Erhardt Krause, both of Hamburg, Germany

[73] Assignee: C.S.S. Container Storage Service Establishment, Hamburg, Germany

[21] Appl. No.: 490,294

[22] Filed: July 22, 1974

[30] Foreign Application Priority Data

July 24, 1973 Germany .............................. 2337988

[51] Int. Cl.² .......................................... G01N 27/16
[52] U.S. Cl. ................................................. 23/254 E
[58] Field of Search ............ 23/254 E, 255 E, 232 E; 73/27 R; 340/237 R

[56] References Cited

U.S. PATENT DOCUMENTS

| | | | |
|---|---|---|---|
| 3,418,914 | 12/1968 | Finkin | 340/237 R X |
| 3,440,017 | 4/1969 | Palmer | 23/254 E |
| 3,609,732 | 9/1971 | Kasahara et al. | 23/254 E X |
| 3,764,270 | 10/1973 | Collier et al. | 23/255 E |
| 3,879,667 | 4/1975 | Kraty et al. | 23/237 C X |

*Primary Examiner*—Robert M. Reese
*Attorney, Agent, or Firm*—Michael J. Striker

[57] ABSTRACT

An individual blows into a chamber having a predetermined volume. In the chamber is mounted a gas cell including a heating conductor for catalytic burning of the alcohol and a probe at a predetermined distance from the heating conductor, both embedded in a ceramic porous shell. The lead-in conductor for the probe is connected to the base of a transistor in a threshold circuit which is responsive to the resistance of the gas cell which in turn decreases with increasing alcohol content. When the resistance is less than a predetermined resistance a relay in the transistor circuit operates, lighting an indicator lamp and, in one embodiment, deenergizing the ignition circuit of a vehicle in which the device is mounted.

1 Claim, 4 Drawing Figures

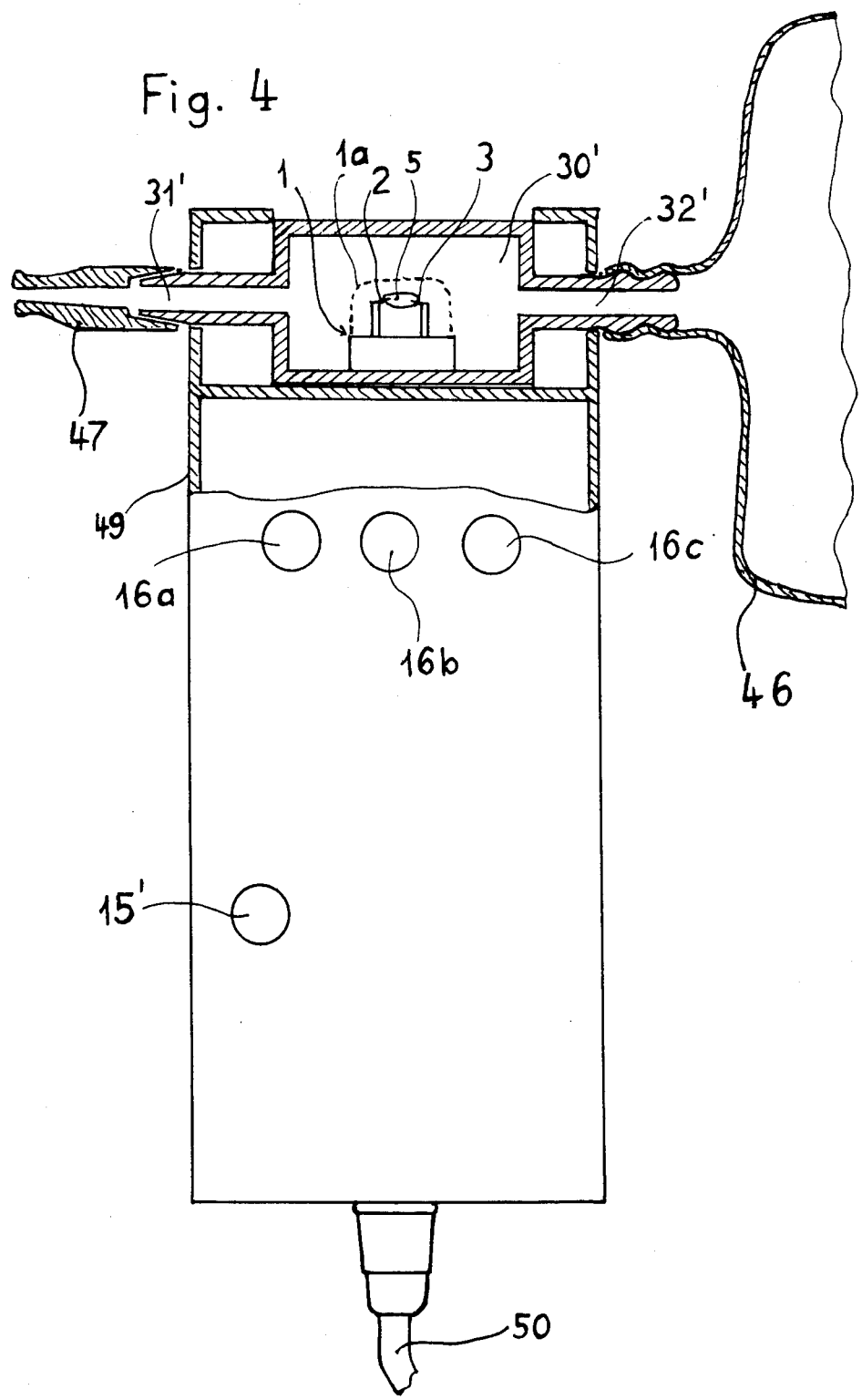

APPARATUS FOR MEASURING THE ALCOHOL CONTENT IN HUMAN BREATH

BACKGROUND OF THE INVENTION

The present invention relates to apparatus for determining the alcohol content in human breath. It is known that the judgment in reaction time of individuals such as, for example, drivers of trucks, is decreased under the influence of alcohol, the decrease being proportional to the alcohol content in the blood. This alcohol content is normally determined by a blood test. The alcohol content in the blood increases to a maximum approximately 1 or 2 hours after the alcohol has been ingested and then decreases slowly. Since, during its circulation, the blood also passes through the lungs and there comes in contact with the air breathed by the individual, the breath of an individual who has had alcoholic drinks will also contain a small amount of alcohol roughly proportional to the alcohol content of the blood. It has therefore been found desirable to determine the alcohol content of the blood rapidly by means of apparatus into which an individual breathes. In known apparatus of this type, the alcohol in the individual's breath causes a chemical reaction which changes the color in the test tube into which the individual breathed, the length of the discoloration increasing with increasing alcohol content. This method is used by the traffic police, but is not particularly accurate.

Furthermore apparatus is known for determining the amount of combustible organic compounds in gas mixtures also containing oxygen. In this apparatus the content of combustible compounds is determined by measuring the heat of reaction resulting from the burning of the combustible compounds by means of a heating conductor. In a known embodiment, two heating conductors are electrically energized and have both a different catalytic effectiveness in the burning process and a different but temperature varying resistance. The two heating conductors are connected to neighboring arms of a wheatstone bridge circuit. Either both of the heating conductors are mounted within the chamber or only one is mounted therein while the other is mounted outside. In each case however the measurement depends on a comparison of the resistance in neighboring arms of a bridge circuit, the heat of reaction of the combustion either influencing both conductors in a different manner or else influencing only one of the conductors so that an unbalanced current proportional to the difference flows in the bridge circuit. In another known embodiment of this type, two heating conductors are arranged in the chamber, each wound on a core of ceramic material and having different catalytic effectiveness for the combustion process. Further associated with each core and connected to the neighboring arm of a wheatstone bridge circuit are two temperature sensitive resistance elements. The unbalanced current of the bridge circuit, which as mentioned above has an amplitude proportional to the content of combustible compounds, is used to generate either warning signals or to activate some switching process. However, the known apparatus is not particularly suitable for many practical applications since it is both complicated and requires a great deal of equipment and on the other hand only yields satisfactory results when all extraneous influences are carefully removed. These extraneous influences in particular include a uniform gas supply and an exact temperature control.

SUMMARY OF THE INVENTION

It is an object of the present invention to furnish apparatus for determining the alcohol content in the human breath which is both readily portable, rugged and does not require much equipment. Further, the apparatus is to furnish a rapid and reliable indication of the actual alcohol content and is to be easily incorporated into the ignition circuit of a motor vehicle in such a manner that the vehicle can only be started after the individual blows into the chamber and then only if the alcohol content of the so-blown air is less than predetermined alcohol content. The present invention comprises a chamber having an inlet and an outlet. It comprises means for furnishing electrical energy and a gas cell. Mounted in the gas cell is a shell of porous ceramic material into which is embedded a heating conductor which is connected to the means for furnishing electrical energy and a probe which is mounted a predetermined distance from said heating conductor. The probe is also connected to the source of electrical energy. The resistance of the gas cell varies as a function of the heat generated by the burning of the alcohol. A probe lead-in conductor is connected to the probe and is further connected to the input of a threshold circuit. The threshold circuit furnishes an excess alcohol signal when the resistance of the gas cell is less than a predetermined resistance.

In a preferred embodiment of the present invention the threshold circuit includes a transistor having a base connected to the probe lead-in conductor and an emitter connected to one terminal of the source for furnishing electrical energy. The connector of the transistor is connected through a relay coil to the other terminal of the means for furnishing electrical energy. The contacts controlled by the relay coil when the relay is energized present the energization of the ignition circuit. Further, an indicator lamp may light indicating an excess alcohol content of the breath.

The construction of the apparatus in accordance with the present invention is very simple and it can readily be utilized as a hand-held apparatus for police testing. It is rugged and furnishes exact measurement values of the alcohol content in a short time period. The apparatus does not require special care and may be used for a long time period for conducting a great number of measurements. If required, the gas cell can be readily replaced. When the apparatus is incorporated into the ignition circuit of a vehicle, the driver is required to blow into the apparatus prior to starting same and is prevented from operating the vehicle when the alcohol content in his breath exceeds a predetermined content.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 4 is a partially sectional view of the arrangement of FIG. 3.

DESCRIPTION OF THE PREFERRED EMBODIMENTS

Figure 1:
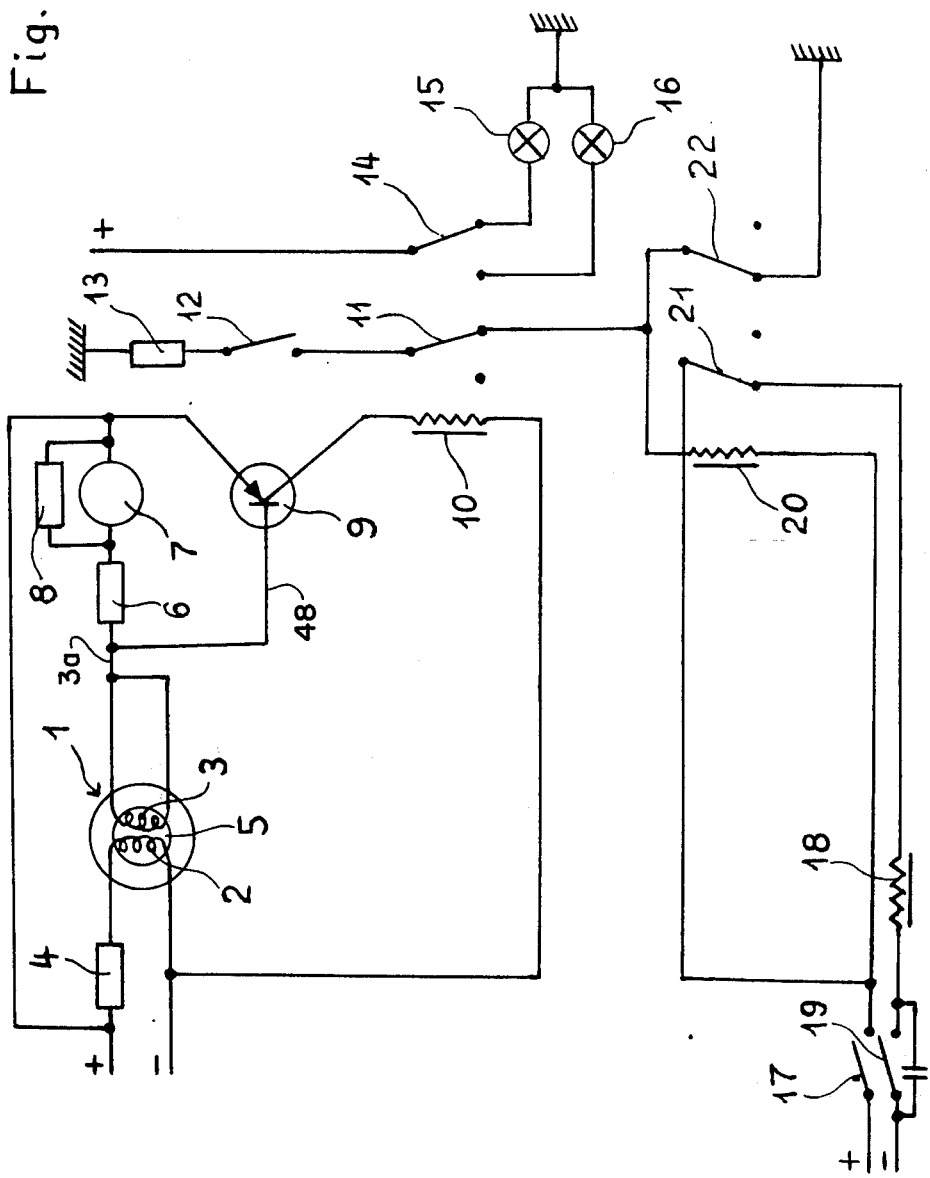
FIG. 1 is a circuit diagram of the present invention when incorporated into the ignition circuit of a motor vehicle.

A preferred embodiment of the present invention will now be described with reference to the drawing.

The apparatus shown in FIG. 1 includes a gas cell 1 having a heating conductor 2 embedded in a porous ceramic shell 5. Heating conductor 2 is connected to a means for furnishing electrical energy, here a 12-volt battery, through a resistor 4 (25 ohms) and, during operation of the apparatus, is heated to a temperature between 300° and 350° C. Also embedded in the ceramic shell 5 at a predetermined small distance from heating conductor 2 is a probe 3 which, as illustrated in a preferred embodiment of the present invention, is a coil whose terminals are short-circuited. A probe lead-in conductor 3a is connected to probe 3. Connected to the probe lead-in conductor is an adjustment resistor 6 (4700 ohms) and a milliammeter 7. Connected in parallel with milliammeter 7 is an adjustment resistor 8. The common terminal of resistor 8, milliameter 7 which is not connected to adjustment resistor 6 is connected to the positive side of the battery. Line 3a is further connected through a line 48 to the base of a transistor 9 whose emitter is directly connected to the positive side of the battery, herein referred to as the first output terminal of the means for furnishing electrical energy. The collector of transistor 9 is connected through coil 10 of a relay, herein referred to as a control relay coil of the negative side of the battery, herein referred to as the second output terminal of the means for furnishing electrical energy. Relay 10 operates a first pair of relay contacts connected by a switch arm 11 and a pair of relay contacts connected by a switch arm 14, herein referred to as the fourth pair of relay contacts. The fourth pair of relay contacts includes a first contact and a second contact connected in the Figure by switch arm 14. When relay 10 is deenergized switch arms 11 and 14 are in the positions shown in the Figure. Under these conditions a lamp 15 connected in series with switch 14 is energized. The lamp is a green lamp indicative of low or no alcohol content. Energization of relay 10 opens the first pair of relay contacts and further causes switch arm 14 to move from the position shown in FIG. 1 to its second position wherein the positive side of the battery is connected to a third contact which in turn is in series with a lamp 16. Lamp 16 is a red lamp which, when lit, indicates excessive alcohol content.

The first pair of relay contacts is connected to a relay coil 20 which herein is referred to as the second relay coil. Relay coil 20 when energized causes closing of the third pair of contacts connected by switch arm 21. Further, when relay coil 20 is energized holding contacts, herein referred to as a pair of second relay contacts, and connected by a switch arm 22 are closed. Closing of contacts 21 is required to establish the circuit from ignition switch 17 through contacts 21 to ignition coil 18 and then through interrupter switch 19 to the other side of the battery. Thus the ignition coil can only receive current when switch arm 21 is in the position shown, that is when relay coil 20 is energized.

The first pair of relay contacts is connected in series with a switch 12 and a resistance 13 whose other terminal is connected to ground.

Figure 2:
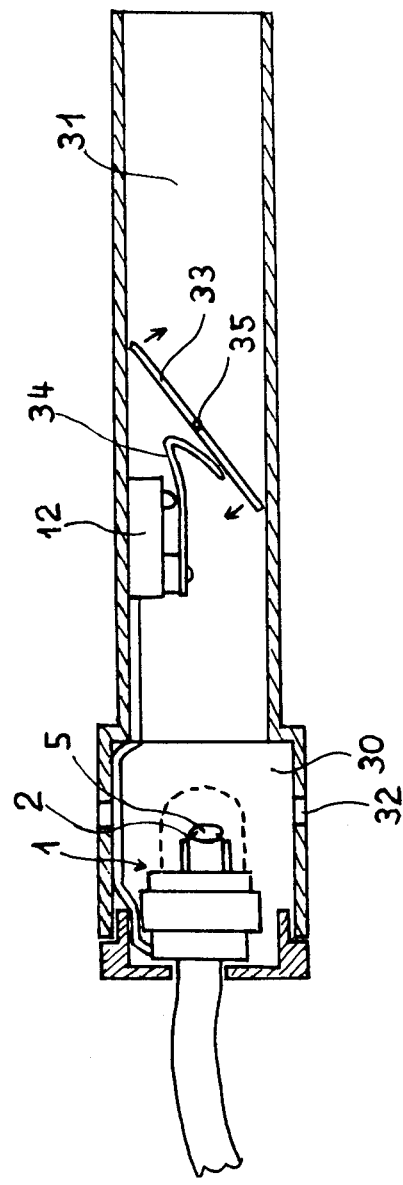
FIG. 2 is a schematic section of the gas chamber.

As shown in FIG. 2, gas cell 1 is mounted in a chamber 30 having an inlet 31 and a plurality of outlets 32. Inlet 31 is of cylindrical shape. Mounted therein is a flap 33 which may be pivoted around an axis 35. As shown in FIG. 2, flap 33 normally closes inlet 31. On one side of flap 33 is a spring 34 which is a weak spring and serves to return flap 33 into its normal position, that is the position shown in FIG. 2. Spring 34 when in the position shown, rests lightly against the contact of a microswitch 12. When the individual blows into inlet 31, flap 33 pivots forcing spring 34 against microswitch 12 thereby closing same.

The apparatus shown in FIGS. 1 and 2 operates as follows:

Before ignition switch 17 is operated, no current flows through relay coils 10 and 20 so that the contacts connected by arm 21 (hereafter referred to as contacts 21) and contacts 22 are open. Microswitch 12 is also open, so that relay 20 would remain deenergized even if ignition switch 17 were closed. The vehicle can thus not be started. The driver is thus forced to blow into inlet 31, his breath moving flap 33 into the position not shown in the drawing so that it reaches into the chamber and to gas cell 1. The pivoting of flap 33 causes a movement of spring 34 which in turn closes microswitch 12. When the blowing ceases, flap 33 returns to its initial position while the breath which has been blown into chamber 30 is retained therein and only slowly diffuses out of the outlets 32. If alcohol is present, this is catalytically burned in the gas cell which has been heated to 330° C. The resultant heat causes the resistance of cell 1 to decrease from, for example, 2000 ohms to, depending on the alcohol content, approximately 200 ohms. The probe lead-in conductor then conducts a weak current which is proportional to the alcohol content in the breath and which is indicated on milliameter 7. When the current in this probe exceeds a predetermined value which is fixed by adjustment resistor 6, transistor 9 conducts sufficient current through relay 10 to open switch 11 and to switch switch 14 to the position wherein indicator 16 is lit. Since microswitch 12 is operated by flap 33 only after the breathed air has reached gas cell 1, the control relay 10 can actuate switch arm 11 before the second relay 20 is energized.

If the alcohol content in the breath and therefore the amplitude of the current in conductor 3a does not exceed the threshold value, relay 10 remains deenergized causing switch 11 to remain closed. Since microswitch 12 is closed resulting from the blowing of air into chamber 30, a current can now flow from ignition switch 17 through relay coil 20, contact 11, switch 12 and resistor 13 to ground. This causes contacts 21 to close and contacts 22 to close. The energization of relay 20 is thus maintained through contacts 22 independent of the position of switch 11, while the connection from the ignition coil to the ignition switch 17 is established through contacts 21. A later opening of switch 12 thus does not prevent the operation of the ignition circuit. Lamps 15 and 16 then of course indicate whether the alcohol content of the breath was below or above the threshold value.

Figure 3:
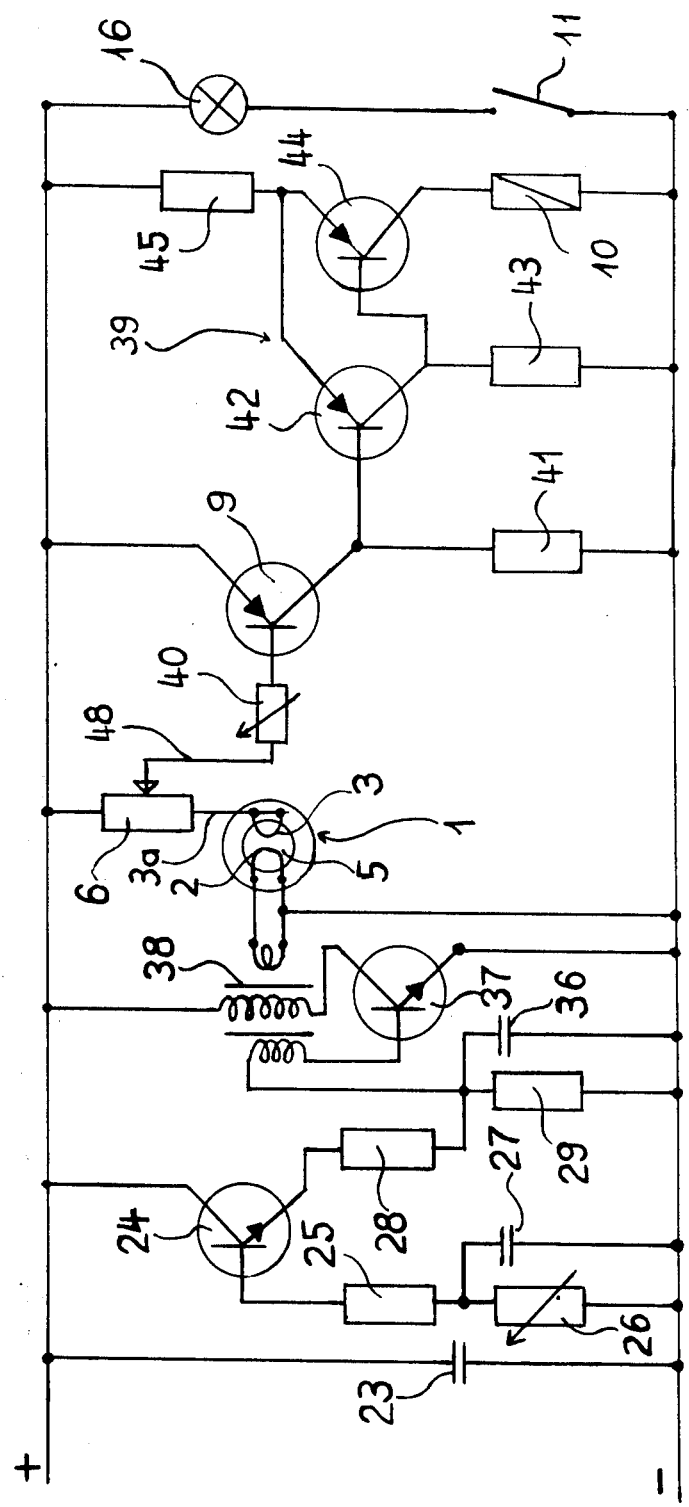
FIG. 3 is a circuit diagram for portable apparatus.

FIGS. 3 and 4 show a portable apparatus in accordance with the present invention. As shown in FIG. 3, a heating conductor again having reference numeral 2 receives its electrical energy through an oscillator stage including a transistor 37 which in turn is energized through a cathode follower stage including a transistor 24. The collector of transistor 24 is directly connected to the positive terminal of a battery while the emitter is connected through a resistor 28 and a capacitor 36 in parallel with a resistor 29 to the negative terminal of the battery. Connected from the positive to the negative battery terminals further is a capacitor 23. The base of transistor 24 is connected through a resistor 25 and a variable resistor 26 connected in parallel with a capacitor 27 to the negative side of the battery. The emitter of transistor 37 is connected to the negative side of the battery while its collector is connected through a transformer 38 to the positive side of the battery. The secondary coil of transformer 38 is connected to the base of transistor 37 and through a resistor 29 connected in parallel with a capacitor 36 to the negative battery terminal. Transformer 38 is also coupled to the heating conductor 2.

As in FIG. 1, gas cell 1 in addition to heating conductor 5 has a probe 3 which, as well as heating conductor 2, is embedded in a ceramic jacket 5. The probe lead-in conductor 3a is connected through a resistor 6 to the positive side of the battery. Adjustment resistor 6 has a variable arm 48 which is connected through a variable resistor 40 to the base of a transistor 9. The emitter of transistor 9 is directly connected to the positive side of the battery while its collector is connected to the negative side through a resistor 41. Also connected to the collector of transistor 9 is the base of a transistor 42 whose emitter is connected through a line 39 and a resistor 45 to the positive side of the battery. Its collector is connected to a resistor 43 whose other terminal is connected to the negative side of the battery. Further, the collector of transistor 42 is connected to the base of a transistor 44 whose emitter is connected in common with the emitter of transistor 42. The collector of transistor 44 is connected through relay coil 10 to the negative side of the battery. The contacts 11 activated by relay coil 10 are connected in series with a lamp 16. The so-formed series circuit being connected across the battery terminals. Transistors 42 and 44 together constitute a Schmitt trigger, transistor 44 constituting the power output transistor and transistor 42 an input transistor for said Schmitt trigger.

For purposes of clarity, only one lamp 16 and its associated Schmitt trigger and transistor 9 are shown in FIG. 3. However, in a preferred embodiment of the present invention the apparatus as shown in FIG. 4 includes lamps 16a, 16b and 16c each of which have an individual transistor 9 and associated Schmitt trigger. Each is individually energized when the current through resistor 6 reaches a predetermined value which is different for the energization of the others of the lamps. Thus a complete circuit diagram of the present invention would include three circuits to the right of resistor 6 in FIG. 3 all being connected to line 48 and each having a different adjustment resistor 40.

The apparatus shown in FIG. 4 includes a chamber 30' having an inlet 31' and an outlet 32'. It also includes a gas cell 1 in which the heating conductor 2 and the probe 3 which are embedded in a ceramic shell 5 are shielded by a wire shield 1a. Chamber 31 is mounted within a housing 49 which contains the electrical circuitry so that inlet 31' and outlet 32' extend beyond said housing. As shown in FIG. 4, the inlet 31' is shaped to receive a mouthpiece 47 so that a different mouthpiece may be used for each individual. Similarly, the outlet 32' allows mounting of a gas-tight bag 46 which has a predetermined volume when fully blown up. Lamps 16a–16c are mounted on one side of the housing and are, respectively, a yellow control lamp, a red control lamp and a blue control lamp. The green lamp 15 is arranged in the lower part of the housing. Electrical energy may be supplied to the arrangement through a cable 50 which allows connection, for example, of the 12-volt battery of a motor vehicle.

The apparatus shown in FIGS. 3 and 4 is particularly suitable for the use of traffic police and can be carried in a patrol car. Thus the apparatus is energized through cable 50 from the battery of the patrol car. It is put into operation by pushing a button (not shown) on one side of housing 49. The apparatus is then ready for operation as soon as lamps 16a–16c are deenergized and the green lamp 15 is energized. For each individual to be tested a new mouthpiece 47 is pushed onto inlet 31 and a new bag 46 is attached to outlet 32'. The individual then blows into mouthpiece 47 until bag 46 is fully blown up. The alcohol in the breath is then catalytically burned by heating conductor 2 and the heat generated thereby causes a decrease in the resistance of gas cell 1 between heating conductor 2 and probe 3. The resistance decreases with increasing alcohol content. By corresponding adjustment of adjustment resistors 6 and resistors 40 associated with the individual control lamps, the apparatus can be so adjusted that for no alcohol content only green lamp 15 lights, for an alcohol content less than 0.8% yellow control lamp 16a lights and green control lamp 15' is extinguished; when alcohol content between 0.8 and 1.2% yellow control lamp 16a and red control lamp 16b light up while for an alcohol content of more than 1.2% yellow control lamp 16a, red control lamp 16b and blue control lamp 16c all light up simultaneously while the green control lamp is extinguished.

Shortly after one measurement has been completed the apparatus is again ready for operation. This is indicated by the extinguishing of control lamps 16a, 16b and 16c and the lighting of the green control lamp 15'.

When the apparatus is first put into operation and a 12-volt voltage is applied thereto, the circuit including transistor 37 starts to oscillate. At first a voltage of 1.2 volts is generated which, after heating conductor 2 has been heated is reduced to a voltage of 0.9 volts by the action of the circuit shown, and in particular by the action of transistor 24, resistance 26 and capacitor 27. However, the latter value can be adjusted as desired. Gas cell 1 with heating conductor 2 heated to a temperature between 300° and 350° C has a temperature variable resistance and, together with resistor 6 constitutes a variable resistance which controls transistors 42 and 44 of the Schmitt trigger. When power transistor 44 becomes conductive, relay 10 serves to close switch 11 and control lamp 16 lights. The lighting of the other lamp 16 takes place in similar fashion each however having a different associated threshold point fixed by its corresponding resistor 40.

It is understood that many variations of the above-described circuitry are possible. In particular instead of one or more control lamps, indicator instruments having a pointer may be used. Electronic switches can be substituted for the relays and the various circuits can be modified in a number of ways readily apparent to one skilled in the art without in any way departing from the basic idea of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A portable hand-held apparatus for determining the alcohol content in the breath of a human subject, comprising, in combination, a gas chamber having an inlet into which the human subject can breathe and having at least one outlet; a low-voltage battery having first and second battery output terminals; first and second D.C. supply lines connected to said first and second battery output terminals; a gas cell mounted in said gas chamber and comprised of a porous semiconductor shell, a heating conductor embedded in said shell and connected to at least one of said supply lines, a probe embedded in said shell at a predetermined distance from said heating conductor, and a probe lead-in conductor connected to said probe, the resistance of said gas cell decreasing with increasing alcohol content of the gas present in said gas chamber; a milliammeter connected between said probe lead-in conductor and said first supply line for measuring and indicating the valve of the alcohol content in said gas; at least one transistor circuit each comprising a transistor and a relay, said transistor having a base connected to said probe lead-in conductor, an emitter connected to said first supply line, and a collector, said relay having a relay coil connected to said collector and said second supply line, at least one pair of relay contacts and at least one switch arm operated by said relay coil; at least one control circuit comprising a control lamp, one pair of said relay contacts being opened and closed by the corresponding relay switch arm and connected to cause said control lamp to light up when the current in the probe lead-in conductor exceeds a value corresponding to a predetermined alcohol content; and an adjustment resistor connected between said probe lead-in conductor and said first supply line and operative for adjusting the value of the probe lead-in conductor current at which said control lamp lights up, whereby a traffic officer or the like operating at night, in the rain, or in other low-visibility conditions, is informed by the control lamp that he should bother to take a precise alcohol content reading and is enabled by the milliammeter to thereafter actually take the reading.

* * * * *

UNITED STATES PATENT AND TRADEMARK OFFICE
CERTIFICATE OF CORRECTION

PATENT NO. : 4,047,893
DATED : September 13, 1977
INVENTOR(S) : Bob Kok and Erhardt Krause It is certified that error appears in the above-identified patent and that said Letters Patent are hereby corrected as shown below:

In the heading [73], the address of the assignee should read -- Vaduz, Liechtenstein --.

Signed and Sealed this

Twenty-fifth Day of April 1978

[SEAL]

Attest:

RUTH C. MASON
Attesting Officer

LUTRELLE F. PARKER
Acting Commissioner of Patents and Trademarks